US00PP16313P2

(12) United States Plant Patent
Olesen

(10) Patent No.: US PP16,313 P2
(45) Date of Patent: Mar. 7, 2006

(54) SHRUB ROSE PLANT NAMED 'POULCOT004'

(50) Latin Name: ***Rosa* hybrid**
Varietal Denomination: Poulcot004

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 45 days.

(21) Appl. No.: 11/001,947

(22) Filed: Dec. 1, 2004

(51) Int. Cl.
*A01H 5/00* (2006.01)

(52) U.S. Cl. ..... Plt./108
(58) Field of Classification Search ..... Plt./108, Plt./107, 150
See application file for complete search history.

*Primary Examiner*—Anne Marie Grunberg
*Assistant Examiner*—June Hwu

(57) ABSTRACT

A new garden rose plant of the shrub rose class which has abundant, red flowers and attractive foliage. This new and distinct variety has shown to be uniform and stable in the resulting generations from asexual propagation.

2 Drawing Sheets

Botanical classification: *Rosa* hybrid.
Variety denomination: 'Poulcot004'.

SUMMARY OF THE INVENTION

The present invention constitutes a new and distinct variety of garden rose plant that originated from a controlled crossing between the female seed parent, an unpatented rose named 'Kormixal' and the male pollen parent; an unnamed seedling.

The two parents were crossed during the summer of 1995, and the resulting seeds were planted in a controlled environment in Fredensborg, Denmark. The new variety is named 'Poulcot004'.

The new variety may be distinguished from its female seed parent by the following combination of characteristics:

1. Flowers of 'Kormixal' are red in coloration while flowers of 'Poulcot004' are a pink red blend.
2. 'Poulcot004' has smaller leaflets than 'Kormixal'.

The new variety may be distinguished from its male pollen parent from the following combination of characteristics:

1. The male pollen parent has white flowers while 'Poulcot004' has red flowers.
2. 'Poulcot004' has fewer flower petals than the male parent plant.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Disease resistance;
4. Profusion of decorative rose hips.

This combination of qualities is not present in previously available commercial cultivars of this type, known to the inventor, and distinguish 'Poulcot004' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcot004' was selected in the spring of 1996 by the inventor as a single plant from the progeny of the aforementioned hybridization.

Asexual reproduction of 'Poulcot004' by traditional budding and rooted cuttings was first done by Mogens N. Olesen in the nursery in Fredensborg, Denmark in July 1996. This initial and other subsequent asexual propagations conducted in controlled environments have demonstrated that the characteristics of 'Poulcot004' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcot004'. Specifically illustrated in the drawings are:

FIG. 1.2; Open flower;

FIG. 1.3; Cluster of flower buds showing quantity of flower buds per stem;

FIG. 1.4; Flower petals, detached and sepals, receptacle, and pedicel;

FIG. 1.5; Mature leaves;

FIG. 1.6; Juvenile growth, depicting foliage, stem, and juvenile thorns;

FIG. 1.7; Juvenile and mature bare stems exhibiting thorns.

DETAILED DESCRIPTION OF THE VARIETY

Figure 1:
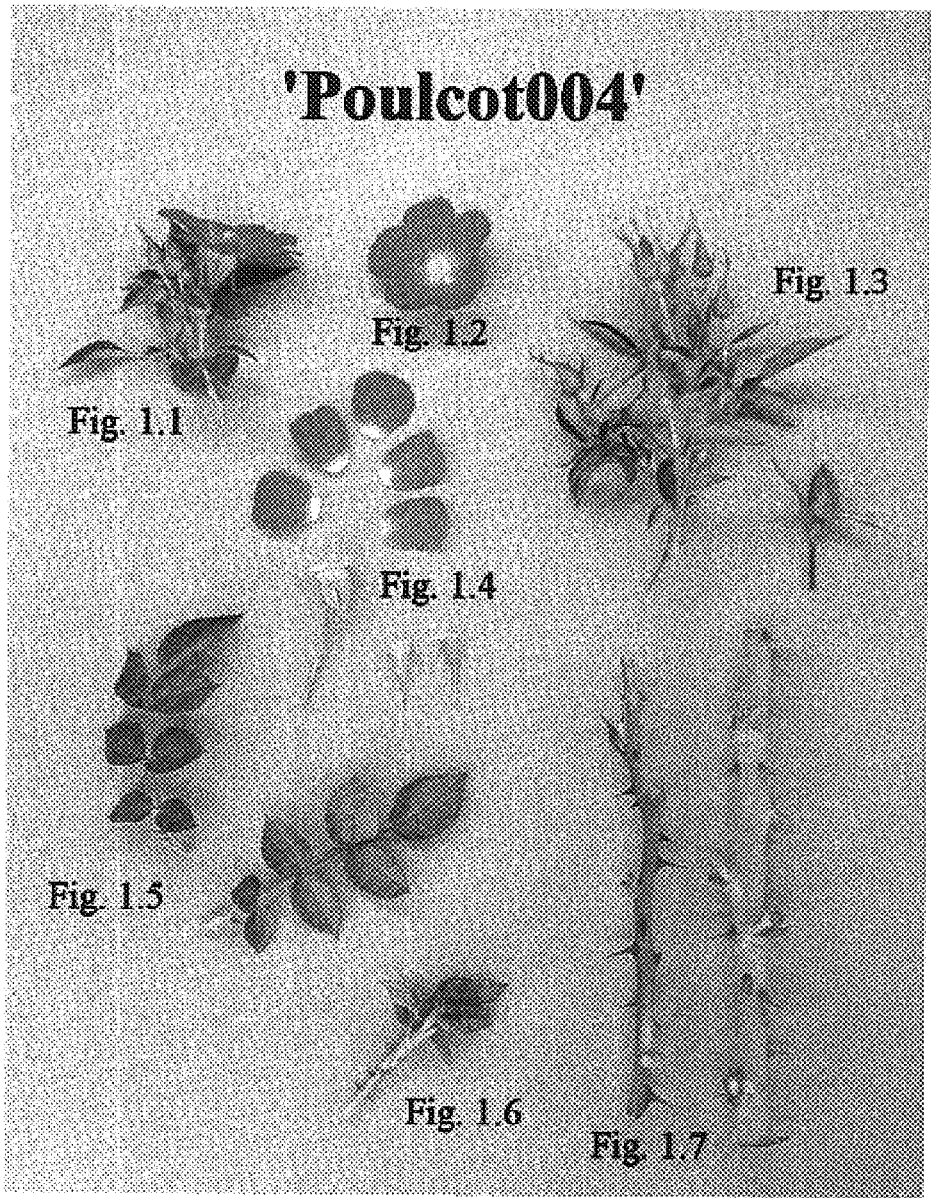
FIG. 1.1; Cluster of flower buds and single open flower attached to stem.
Figure 2:
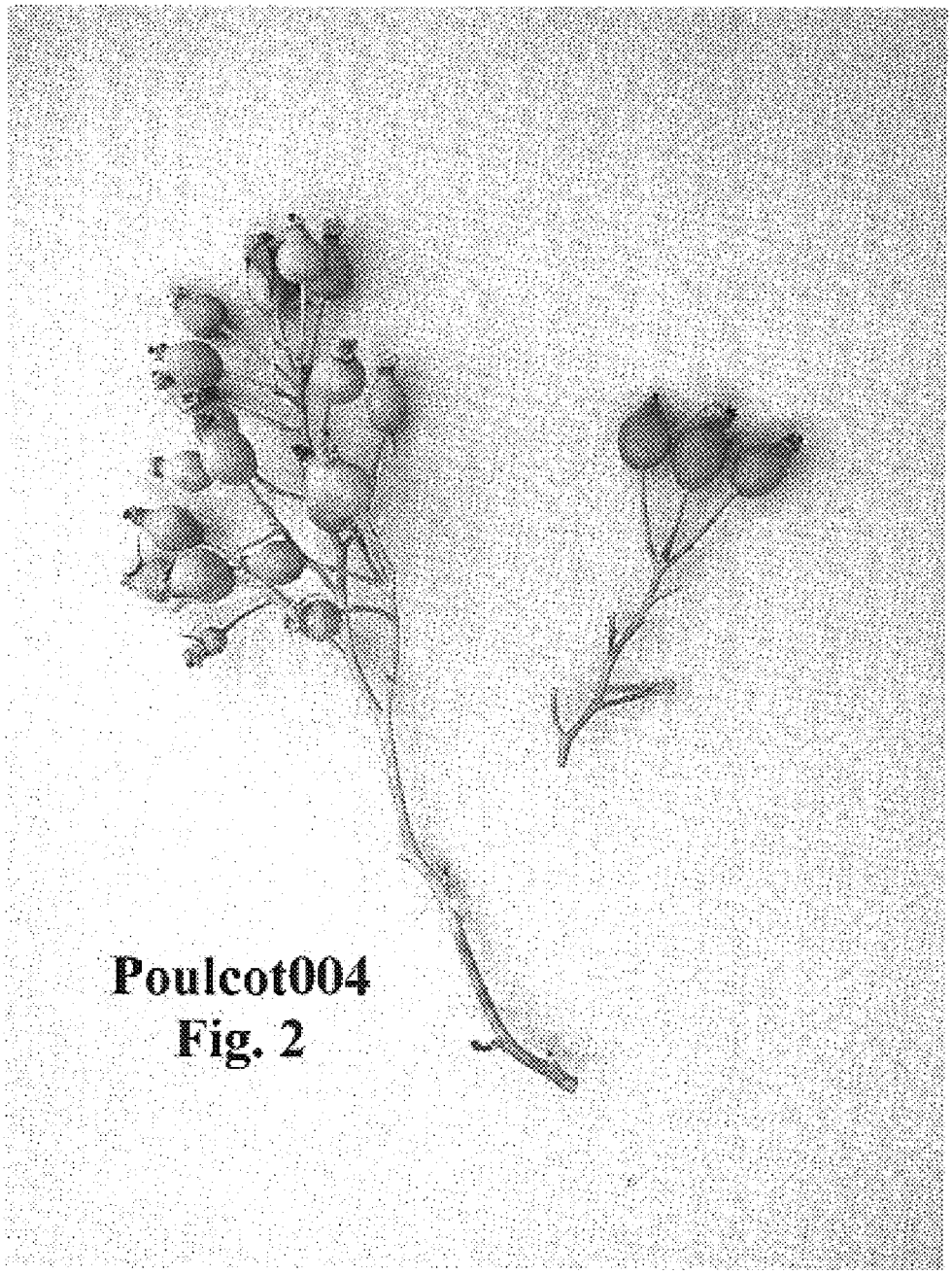
FIG. 2; Rose hips.

The following is a description of 'Poulcot004', as observed in its growth in a field nursery in Jackson County, Oreg. Observed plants are 2 years of age, and were grown on *Rosa multiflora* understock. Color references are made using The Royal Horticultural Society (London, England)

Colour Chart, 2001, except where common terms of color are used.

For a comparison, several characteristics of the rose variety 'Poulrijk', a rose variety from the same inventors described and illustrated in U.S. Plant Pat. No. 12,519 issued Apr. 2, 2002, are compared to 'Poulcot004' in Chart 1.

CHART 1

| | 'Poulcot004' | 'Poulrijk' |
|---|---|---|
| General tonality | Red-Purple Group 57A to 57B | Red-Purple Group 58C |
| Flower bud color when sepals first unfold | Red-Purple Group 57A | Red-Purple Group 58C to D |
| Petalage | 5 to 7 petals | 20 to 25 petals |

FLOWER AND FLOWER BUD

Blooming habit: Continuous.

Flower bud:

*Size.*—Upon opening, 16 mm in length from base of receptacle to end of bud. Bud diameter is 7 mm.

*Bud form.*—Ovate.

*Bud color.*—As sepals unfold, petals are Red-Purple Group 57A.

*Sepal inner surface.*—Color: Yellow-Green Group 145A to Yellow-Green Group 146B. Surface: Weakly pubescent.

*Sepal outer surface.*—Color: Yellow-Green Group 146B. Texture: Rough with stipitate glands.

*Sepal shape.*—Apex: Cirrhose. Base: Flat at union with receptacle.

*Sepal margin.*—Margins have medium to weak foliaceous appendages on three of the five sepals.

*Sepal size.*—22 mm (l)×6 mm (w).

*Receptacle.*—Texture: Smooth and glabrous. Shape: Pear shaped. Size: 5 mm (h)×4 mm (w). Color: Yellow-Green Group 144A to Green Group 138B.

*Peduncle.*—Surface: Smooth. Length: 12 to 24 mm. Diameter: 3 mm on average. Color: Yellow-Green Group 144C.

*Pedicel.*—Surface: Very rough with stipitate glands. Length: 12 to 14 mm on average. Diameter: 1.5 mm on average. Color: Yellow-Green Group 144B to Green Group 143B. Anthocyanic pigments Greyed-Red Group 182A. Strength: Weak.

Flower bud development: Flower buds are borne in clusters of 5, resembling a thyrse. Flower clusters occur every 15 to 20 mm along the peduncle.

Flower bloom:

*Fragrance.*—None.

*Duration.*—The blooms have a duration on the plant of approximately 7 to 10 days. Petals fall cleanly away from plant after flowers have fully matured.

*Size.*—Flower diameter is 37 mm when open. Flower depth is 10 mm.

*Flower shape.*—When fully open, flowers are nearly flat.

*Shape of flower, side view.*—Upon opening: Upper portion: Flat. Lower portion: Flattened convex. After opening: Upper portion: Flat. Lower portion: Flattened convex.

*Petalage.*—Flowers have 5 to 7 petals.

*Petal color.*—Upon opening: Upper surface: Red-Purple Group 57A to 57B. Lower surface: Red-Purple Group 58B. Basal petal spots, upon opening: Upper surface: White Group 155B. Green-White Group 157A at point of attachment. Lower surface: White Group 155B. Green-White Group 157A at point of attachment. After opening: Upper surface: Red-Purple Group 57A to 57B. Lower surface: Red-Purple Group 58B. Basal petal spots, upon opening: Upper surface: White Group 155B. Green-White Group 157A at point of attachment. Lower surface: White Group 155B. Green-White Group 157A at point of attachment.

General tonality: On open flower Red-Purple Group 57A to 57B. After flowers have remained open 5 to 6 days color fades to Red-Purple 58B.

Petals:

*Petal reflex.*—Flat.

*Margin.*—Entire, point at the center observed.

*Shape.*—Narrow elliptic. Apex: Cuspidate. Base: Acute.

*Size.*—19 mm (l)×15 mm (w).

*Texture.*—Smooth.

*Thickness.*—Thin.

Reproductive organs:

*Pollen.*—None observed.

*Anthers.*—Size: 1 mm in length. Color: Greyed-Orange Group 167A. Quantity: 100 on average.

*Filaments.*—Color: Yellow-Green Group 150C. Length: 3 to 5 mm.

*Pistils.*—Length: 2 to 3 mm. Quantity: 20 to 25.

*Stigmas.*—Inferior in location relative to the length of the filaments and the height of the anthers. Stigmas are tightly arranged at flower center. 2 to 3 cm space between stigmas and surrounding anthers. Color: Yellow-Green Group 150C to Greyed-Orange 163B.

*Styles.*—Color: Green-White Group 157A.

*Hips.*—Color: Greyed-Orange Group 168A. Size: 16 mm (h)×10 mm diameter. Shape: Elliptical.

PLANT

Plant growth: Spreading and low growing. When grown as a budded field grown plant on *Rosa multiflora* understock, the average height of the plant is 40 to 60 cm and the average width is 40 to 60 cm.

Stems:

*Color.*—Juvenile growth: Green Group 143D. Anthocyanic intonations of Greyed-Orange Group 174A. Mature growth: Green Group 143D.

*Length.*—On average, canes are 40 to 60 cm from the base of the plant to the flowering portion.

*Diameter.*—4.5 mm.

*Internodes.*—On mature canes, there is an average distance of 20 mm between nodes.

*Surface texture.*—Young wood: Smooth. Older wood: Smooth.

Thorns:

*Incidence.*—15 thorns per 10 cm of stem on average.

*Size.*—8 mm.

*Shape.*—Upper side: Flat. Lower side: Concave.

*Color.*—Juvenile and mature thorns are Greyed-Red Group 181A.

Plant foliage: 7 leaflets on normal leaves at the middle of the stem.

*Compound leaf.*—90 mm (l)×50 (w).

*Quantity.*—5 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 144A, margins are Greyed-Red Group 180A. Lower side: Yellow-Green Group 144A.

Plant leaves and leaflets:

*Stipules.*—Size: 17 mm in length. Shape: Linear, slightly broad based with outward extending apecies. Margins: Finely serrated with stipitate glands. Color: Yellow-Green Group 146A.

*Petiole.*—Length: 20 mm. Diameter: 2 mm.

*Upper surface.*—Color: Greyed-Red Group 181A. Observations: Few stipitate glands.

*Lower surface.*—Color: Yellow-Green Group 146C. Observations: Few stipitate glands. Few small prickles.

*Rachis.*—Length: 40 mm. Upper surface: Color: Yellow-Green Group 146A. Observations: Few stipitate glands. Lower surface: Color: Yellow-Green Group 146C. Observations: Small prickles.

*Leaflet.*—Edge: Serrated. Size: Average size of the terminal leaflet on normal leaves is 33 mm (l)×19 mm (w). Shape: Lanceolate to ovate. Base: Acuminate. Apex: Acuminate. Texture: Smooth. Thickness: Average. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'Poulcot004' has been found to be cold tolerant to USDA Cold Hardiness Zone 6.

It is claimed:

1. A new and distinct variety of rose plant of the shrub rose class named 'Poulcot004', illustrated and described herein as a distinct and novel rose variety due to its abundant red flowers, plentiful rose hips, exceptional disease resistance, and extended period of bloom.

* * * * *

'Poulcot004'
Fig. 1.1
Fig. 1.2
Fig. 1.3
Fig. 1.4
Fig. 1.5
Fig. 1.6
Fig. 1.7

Poulcot004